United States Patent [19]

Lask et al.

[11] 4,248,595
[45] Feb. 3, 1981

[54] PROCESS FOR PREPARING SWELLABLE CROSS-LINKED CARBOXYALKYLCELLULOSES, IN THE FORM OF FIBERS, FROM CELLULOSE HYDRATE AND USE THEREOF

[75] Inventors: Helmut Lask; Arno Holst, Wiesbaden, both of Fed. Rep. of Germany

[73] Assignee: Hoechst Aktiengesellschaft, Fed. Rep. of Germany

[21] Appl. No.: 43,543

[22] Filed: May 29, 1979

[30] Foreign Application Priority Data

May 31, 1978 [DE] Fed. Rep. of Germany ....... 2823757

[51] Int. Cl.³ .................... C08G 59/00; C08B 17/00
[52] U.S. Cl. ........................................ 8/116 P; 8/120; 8/181; 8/194; 536/84; 536/87; 536/88; 536/98
[58] Field of Search .............. 8/116 P, 194, 181, 120, 8/116 P; 536/87, 88

[56] References Cited

U.S. PATENT DOCUMENTS

| | | | |
|---|---|---|---|
| 2,101,263 | 12/1937 | Maxwell | 8/120 |
| 2,553,725 | 5/1951 | Rogers et al. | 536/85 |
| 3,589,364 | 6/1971 | Dean et al. | 8/116.2 |
| 3,723,413 | 3/1973 | Chaterjee et al. | 536/87 |
| 3,936,441 | 2/1976 | Holst et al. | 536/44 |
| 3,965,091 | 6/1976 | Holst et al. | 536/87 |
| 3,997,647 | 12/1976 | Lassen | 8/116 P |
| 4,066,828 | 1/1978 | Holst et al. | 536/88 |
| 4,068,068 | 1/1978 | Holst et al. | 536/88 |
| 4,075,279 | 2/1978 | Holst et al. | 536/88 |
| 4,136,218 | 1/1979 | Nischwitz et al. | 427/339 |
| 4,187,342 | 2/1980 | Holst et al. | 428/283 |

FOREIGN PATENT DOCUMENTS

| | | |
|---|---|---|
| 2710874 | 9/1978 | Fed. Rep. of Germany . |
| 1346293 | 11/1963 | France . |
| 1492040 | 11/1977 | United Kingdom . |

Primary Examiner—A. Lionel Clingman
Attorney, Agent, or Firm—James E. Bryan

[57] ABSTRACT

This invention relates to a process for preparing swellable cross-linked carboxyalkylcelluloses in the form of fibers, by reacting cellulose, a carboxyalkylating etherifying agent, and a cross-linking agent in an aqueous alkaline medium, comprising effecting alkalizing, etherifying, and cross-linking simultaneously in one reaction step using fibers of cellulose hydrate or fiber-based textile sheet materials which contain these fibers, by contacting said fibers or textile sheet materials which contain these fibers with an ample quantity of an aqueous alkaline reaction mixture, removing part of the reaction mixture from the fibers or the textile sheet materials contacted therewith, so that at least the quantity required for reaction is still present, and treating the fibers or the textile sheet materials containing the remainder of the aqueous alkaline reaction mixture with heat energy.

7 Claims, No Drawings

PROCESS FOR PREPARING SWELLABLE CROSS-LINKED CARBOXYALKYLCELLULOSES, IN THE FORM OF FIBERS, FROM CELLULOSE HYDRATE AND USE THEREOF

The present invention relates to a process for preparing swellable, cross-linked carboxyalkylcelluloses in the form of fibers, from cellulose hydrate and to the use of products prepared according to this process, particularly in the manufacture of non-woven fabrics.

Recently, swellable carbohydrate derivatives, for example, swellable cross-linked cellulose ethers, particularly carboxyalkylcelluloses, have increasingly gained significance in all fields in which physiological fluids, for example, urine, blood, perspiration, or saliva must be absorbed, namely in infant care, female hygiene, and for the purposes of medical practices and hospitals. They are either incorporated as additions in the absorptive compositions used, e.g., in tampons, sanitary pads, non-woven fabrics, baby's napkins, or under-blankets, which frequently have cellulose as a base material, or they are the sole constituents of these compositions.

Further, these swellable substances are used to improve the absorption capacity for water vapor of binder-treated non-woven fabrics which are of interest for various technical applications. These applications include the use of the non-woven fabrics as substitutes, particularly for leather or certain textiles which are, for example, employed in the manufacture of shoes (shoe uppers, linings, soles), bags, upholstery covers, outer garments ("leather" and all-weather garments) or for textiles and articles for domestic use (table cloths, window "leathers", wiping cloths). They are, however, also used in combination with or as complements to the materials (e.g. leather or textiles) which may be employed for the above-mentioned purposes, apart from the non-woven fabrics.

Other possible applications for these swellable substances are in the manufacture of sheet materials which are capable of absorbing and transmitting water vapor and are prepared from various natural or synthetic polymers, for example, polyvinyl chloride, polyurethane, rubber, polyalkylenes, cellulose hydrate etc. These sheet materials which may have, for example, the form of self-supporting films or of coatings on substrates are, particularly, suitable as leather substitutes (synthetic leather) for use as shoe uppers, upholstery covers, bags, and outer garments ("leather" and all-weather garments), or as covering materials, e.g., tent materials or tarpaulins.

Various processes are known for preparing swellable carbohydrate derivatives, e.g., swellable cross-linked cellulose ethers. Among these are, especially, the following: German Offenlegungsschrift No. 1,912,740 (corresponding to U.S. Pat. No. 3,589,364) describes carboxymethylcellulose fibers which are suitable for use in fiber materials absorbing and retaining aqueous solutions and which are substantially insoluble in water. They are wet-cross-linked fibers of originally water-soluble salts of carboxymethylcellulose (CMC) having a degree of substitution (DS) of about 0.4 to 1.6, and they have the original structure of the cellulose fibers. They are either prepared in a single reaction step in which the cellulose is simultaneously carboxymethylated and wet-cross-linked, or in two reaction steps in which the cellulose is first wet-cross-linked and then carboxymethylated. The initial substance used for the reaction is natural or regenerated cellulose; the cross-linking agent is caused to act under alkaline or acid conditions. Among the various cross-linking agents, epichlorohydrin is preferred. The cellulose fibers are suspended in an inert organic diluent, for example, isopropanol, in the presence of a small amount of water, and are caused to react under alkaline conditions with about 3 to 10% by weight of the cross-linking agent. The amount of the inert organic diluent used corresponds to about 40 times the amount of cellulose.

German Offenlegungsschrift No. 2,364,628 discloses a structure, rendered hydrophilic, of a fiber-forming and a film-forming water-insoluble polymer, which contains particles of modified cellulose ethers which are such that if only etherification were carried out to the given extent, water-soluble cellulose ethers would result, but which are modified in such a way that, at least for the major part, they are water-insoluble but retain the capacity to absorb water. The structures, rendered hydrophilic, are, particularly, films but also filaments, provided they are prepared in a usual precipitation process, e.g., from regenerated cellulose. The pulverulent or granular material composed of the modified cellulose ethers is, for example, added to the polymer composition and is uniformly distributed therein prior to forming.

A process for improving the absorption of water and the absorptivity of fiber materials composed of or containing synthetic fibers or filaments is described in German Offenlegungsschrift No. 2,441,781. In this process, modified highly-absorbent cellulose ethers are fixed to the fiber materials with the aid of finishing agents, permanent-finishing agents, resins, or binders. The modified cellulose ethers are, together with the agents serving to fix them to the fiber material, applied to the latter from aqueous preparations, such as solutions, dispersions, or emulsions. A cellulose ether modified with N-methylol acrylamide is preferably used, in an amount of about 0.1 to 5% relative to the weight of the improved fiber material.

In the process for the preparation of highly-absorbent cellulose filaments according to German Offenlegungsschrift No. 2,447,282 (corresponding to U.S. Pat. No. 3,997,647) modified cellulose fibers are caused to swell in a liquid, so that they can be extruded in the swollen condition; during extrusion the fibers are oriented, and they combine to form filaments. The filaments are then dried to neutralize the swollen intermediate condition of the fibers and to allow the formation of capillary-type longitudinal channels within the filaments. By "modification of the cellulose" a chemical substitution, a chemical substitution and cross-linking, or a graft-polymerization is to be understood.

German Offenlegungsschrift No. 2,519,927 (corresponding to U.S. Pat. No. 4,068,068) discloses a process for the preparation of cellulose ethers which absorb water, but are to a large extent insoluble in water. In this process, cellulose is, in the presence of an alkali, reacted with an etherifying agent in such a way that a water-soluble cellulose ether would result, if etherification only were carried out. Prior to, simultaneously with, or after etherification of the cellulose cross-linking with bisacryl-amido-acetic acid is effected. The cellulose is alkalized in a first step, and in a second, and if necessary in a third step, the other reaction components are, successively or together, added to the alkali cellulose in the presence of 0.8 to 7.5 parts by weight of isopropanol, relative to the weight of the cellulose, and are caused to react for about 1 hour at a temperature of about 50° to 80° C. The last-mentioned reaction also may be performed directly with the alkali cellulose which is moist with water, without the addition of isopropanol, provided the existing mixture of powder or crumbs is loose and does not stick together.

A similar way of carrying out the reaction without any organic diluent also has been disclosed in German Offenlegungsschrift No. 2,520,337 (corresponding to U.S. Pat. No. 4,066,828). The cross-linking agents used are acrylamidomethylene chloroacetamide, dichloroacetic acid, phosphorus oxychloride, or compounds of a type, which as groups which are reactive towards cellulose in alkaline media, contain at least two of the acrylamido group, the chloroazomethine group, or the allyloxyazomethine group.

German Offenlegungsschrift No. 2,543,187 describes another method of effecting the reaction without any organic diluent. In this method, clippings from lacquered or unlacquered cellulose hydrate films are alkalized in a first step, and are then etherified using a halogen fatty acid, for example, monochloro-acetic acid, and reacted with a polyfunctional cross-linking agent.

German Offenlegungsschrift No. 2,710,874, describes a process in which rayon staple fibers are placed in a reactor equipped with a pump circulating system for solvents and are alkalized with an about 50% concentration aqueous NaOH solution, in the presence of about 13 parts by weight of an 87% concentration isopropanol per part by weight of fibers. Then the alkalized rayon staple fibers are etherified with Na-monochloroacetate and simultaneously cross-linked with bisacrylamidoacetic acid for about 1 hour at a temperature of about 70° C. Upon completion of the reaction, the mixture is neutralized and filtered, and the solid residue composed of cross-linked etherified rayon staple fibers is washed free from salt in an aqueous alcohol. The fiber material obtained has a good absorption and retention capacity for water and is water-insoluble to the extent of about 70%.

The processes known from prior art have, however, various disadvantages:

In all preparation processes, alkalizing is carried out separately and, thus, in a time-consuming manner, prior to the etherifying and/or cross-linking reaction.

The more or less important quantities of organic diluents used require expensive special apparatus in order to recover these diluents or to reprocess them in an ecologically acceptable way, and also to meet the stringent requirements with respect to the operational safety of the processes in which these diluents are employed.

In the processes which are carried out without adding any organic diluents, the course of the reaction is often very irregular, because the mixture of powder or crumbs used makes it difficult for the reaction components to reach all reactive areas of the cellulosic material.

The application of absorbent modified cellulose ethers or similar substances to the surfaces of fibers, or the incorporation of these substances in the raw material mass used for preparing the fibers, often renders difficult the further processing of the components brought together. In addition, it is inconvenient that the absorbing capacity of the modified cellulose ethers added is reduced either by the auxiliary agents used to facilitate the application, or during the fiber production from the component mixture.

The preparation of fibers and/or filaments directly from modified cellulose derivatives normally can be carried out only using cellulose derivatives which are not too highly swellable, because otherwise the fiber and/or filament production is rendered difficult by the swelling liquids.

It is, therefore, an object of the present invention to provide a process for preparing cross-linked carboxyalkylcelluloses, which does not require a great amount of expensive apparatus and provides fibers or textile sheet materials containing these fibers, which have a good swelling capacity.

The invention is based on the process for preparing swellable cross-linked carboxyalkylcelluloses in the form of fibers, by reacting cellulose, a carboxyalkylating etherifying agent, and a cross-linking agent in an aqueous, alkaline medium. The process of the invention has the feature that alkalizing, etherifying, and cross-linking are carried out simultaneously in one reaction step, using fibers of cellulose hydrate or fiber-based textile sheet materials which contain these fibers; the fibers or the textile sheet materials containing these fibers are first contacted with an ample quantity of an aqueous alkaline reaction mixture, then part of the reaction mixture is removed again from the fibers or textile sheet materials contacted therewith, so that at least the quantity required for reaction is still present, and the fibers or textile sheet materials containing the remainder of the aqueous alkaline reaction mixture are treated with heat energy.

Swellable carboxyalkylcelluloses are those which swell when they are immersed in aqueous liquids, particularly liquids containing more than 50% by weight of water, or when they come, in another way, into contact with water molecules (for example, water vapor); they are water-insoluble to the extent of at least about 30% by weight, particularly of at least about 50% by weight. The carboxyalkylcelluloses prepared according to the present invention are in the form of fibers having lengths of about 1 mm to about 200 mm, particularly of about 10 mm to about 150 mm.

The process of the invention is, especially, carried out in such a way that the fibers of cellulose hydrate or the textile sheet materials containing these fibers are sprayed with or immersed in the aqueous alkaline reaction mixture which contains the aqueous solution of an alkalizing agent and, in addition, already the carboxyalkylating etherifying agent and the cross-linking agent. This process step is, among others, performed to achieve a good mixing of the fibers with the reaction mixture, because producing a uniform contact between the fibers and the other reaction components will yield the advantage of a uniform course of the reaction, i.e. an as far as possible homogeneous substitution on the cellulose molecules can be obtained.

For the purpose of the actual chemical reaction the excess quantity of the reaction mixture is then removed again from the fibers or textile sheet materials contacted therewith. This may particularly be done by squeezing off or centrifuging. The excess quantity is, maximally, the quantity which is not required for the chemical reaction of the cellulose with the aqueous mixture composed of the alkalizing, etherifying, and cross-linking agents; appropriately it amounts to a multiple of the quantity which is actually required for reaction, for example, 5 to 50 times the quantity. To effect the chemical reaction between the participants in the reaction, the mixture composed of the fibers or the textile sheet materials and the remainder of the reaction mixture is treated with heat energy. Heat energy is, appropriately, applied in the form of hot air, for example, in a drying apparatus (e.g., a drying chamber) equipped with an air circulating system, or in another type of equipment wherein hot air streams through the material to be treated; or heat energy is generated by means of microwaves. If microwaves are employed, the heat is not supplied from the outside, as in the case of the other process variants mentioned, but it is generated directly on the fibers, i.e. at the place of the actual chemical reaction.

The required reaction times depend, among others, upon the transmission of heat through the fibers, that is to say, the better the heat transfer, the shorter the reaction time. The required reaction times range between about 15 seconds and about 60 minutes, depending upon the way in which the heat energy is supplied. If hot air is used, the reaction time ranges, for example, from about 4 minutes to about 60 minutes, at a temperature of the hot air of about 70° C. to about 160° C. If, on the other hand, microwaves are employed, the reaction time ranges from about 15 seconds to about 60 seconds.

For economic reasons, an aqueous NaOH solution is nearly always used as the alkalizing agent for the cellulose hydrate when carrying out the process of the invention. Other aqueous alkaline solutions, for example, KOH or LiOH solutions, are, however, also suitable as alkalizing agents. The concentrations of the aqueous solutions may vary within wide limits, appropriately, they range from about 10 to 60% by weight.

As the carboxyalkylating etherifying agents monochloroacetic acid or the salts thereof are preferred, but monochloropropionic acid or acrylamide also may be used, and then the carboxyalkylation is a carboxyethylation, or, preferably, a carboxymethylation and results in a carboxymethyl cellulose (CMC) or a carboxyethyl cellulose (CEC). If the process of the invention were carried out without the mandatory cross-linking, the degrees of substitution (DS) of the resulting cellulose ethers would be such that the latter would be at least partially water-soluble.

Apart from the etherifying reaction, cross-linking is carried out in the process according to the invention, and cross-linking results in products which absorb comparatively large quantities of water and are also capable of retaining these quantities more or less well, without dissolving completely themselves. The below-mentioned cross-linking agents are preferred for this purpose; of these, particularly, 0.0005 to 0.2 part by weight should be used, relative to 1 part by weight of the cellulose hydrate. They are compounds carrying at least one of the following functional groups reactive towards hydroxyl groups:

the acrylamido group, $R_1$ being H or $CH_3$ 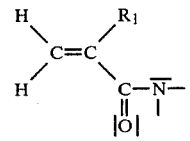

an α halogenoepoxy group, Hal being Cl or Br 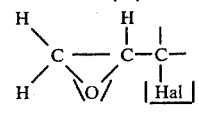

the chloroazomethine group 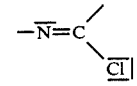

and the allyloxy-azomethine group 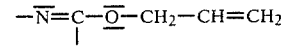

The cross-linking agent also may be phosphorus oxychloride or acrylamido-methylene chloroacetamide. Dichloro-acetic acid which also may be employed as a cross-linking agent should, however, be used in a quantity of at least 0.01 part by weight per part by weight of the cellulose hydrate.

The following are exemplary of compounds carrying the functional groups mentioned:
methylene bisacrylamide,
bisacrylamido-acetic acid,
N,N'-dimethylol-methylene-bisacrylamide,
1,1-bisacrylamido-ethane,
methylene-bismethacrylamide,
epichlorohydrin,
2,4,6-trichloro-pyrimidine,
2,4,5,6 tetrachloro-pyrimidine,
cyanuric chloride,
triallyl-cyanurate.

The cellulosic starting material used in the process of the invention is composed of fibers of cellulose hydrate, i.e. fibers of regenerated cellulose (for example, viscose, i.e. fibers prepared from cellulose sodium xanthogenate). Preferably, so-called rayon staple fibers are used, i.e. fibers of cellulose hydrate which have been cut as uniformly as possible and have lengths ranging from about 30 to about 150 mm, particularly from about 30 to about 60 mm. The cellulose hydrate fibers, however, also may be in the form of a finished textile sheet material, for example, a woven or a non-woven fabric, in which these fibers may not be only exclusively present, but also may be blended with other fibers, for example, fibers of a natural cellulose, such as cotton, or synthetic fibers, such as polyester fibers.

Appropriately, the molar relationships of the components to be used in the process according to the invention range from about 0.7 to 2.1 moles of alkali hydroxide, 10 to 30 moles of $H_2O$, 0.7 to 2 moles of the etherifying agent, and 0.005 to 0.1 mole of the cross-linking agent (relative to 1 mole of cellulose).

The process of the invention yields products which may be prepared by means of technologically simple equipment, because there is, for example, no need for explosion-proof equipment parts. In addition, the reaction time may be reduced, because the process allows a combination of alkalizing, etherifying, and cross-linking in one reaction step. By contacting the fibers or the textile sheet materials with considerable quantities of the reaction mixture a good reaction behavior is ensured; the actual chemical reaction is then carried out with the required quantity of the reaction mixture only. Among others, it is thus possible to save energy and to use equipment which is not excessively large.

The fibers or the textile sheet materials containing these fibers, which are prepared according to the process of the invention are, especially, used in the production of non-woven fabrics. The other aforementioned applications are, however, also feasible. Further details with respect to the incorporation of swellable fibers in non-woven fabrics or sheet materials based on polymer compositions are disclosed in the following publications:

German Offenlegungsschriften Nos. 2,756,671 (incorporation in polyurethane), 2,756,484 (incorporation in polyvinyl chloride), 2,710,874 (incorporation in nonwoven fabrics), 2,736,205 (incorporation in rubber), and 2,736,147 (incorporation in adhesives).

The parameters used in the description and in the examples to characterize the carboxyalkylcelluloses prepared according to the invention are defined as follows:

WRV Water retention value of the swellable cross-linked polymer in % by weight, measured against 1,600 times the acceleration due to gravity, relative to its water-insoluble fraction; WRV is determined after immersing the sample in water.

WUA Water-insoluble fraction in the swellable cross-linked polymer.

DS Degree of substitution, i.e. the average number of substituted hydroxyl groups on the anhydro-D-glucose units, from 0.0 to 3.0.

EXAMPLE 1

40 g of rayon staple fibers (1.7 dtex, length 40 mm) are immersed for 5 minutes at room temperature in a solution composed of 92.7 g of NaOH, 270 g of Na-monochloroacetate, 11.46 g of bisacrylamido-acetic acid, and 626 g of $H_2O$, and are then treated in a centrifuge to yield a reaction weight (fiber+reaction mixture) of 125 g. To effect the actual chemical reaction (alkalizing, etherifying, and cross-linking), the mixture is stored for 30 minutes in a drying chamber heated to 80° C. After neutralizing with hydrochloric acid the reaction product is filtered, and the solid residue is washed free from salt in a 70% by weight aqueous methanol. The fiber material dried at a temperature of about 60° C. has the following parameters:

WRV=1,560, WUA=69, and DS=0.29.

EXAMPLE 2

The procedure is the same as in Example 1, but in this case 22 g of the fibers are immersed in a solution composed of 60 g of NaOH, 175 g of Na-monochloroacetate, 5.94 g of bisacrylamido-acetic acid, and 459 g of $H_2O$; the fibers are centrifuged to a reaction weight of 75.7 g. The reaction time is 60 minutes at a temperature of 80° C. The fiber material has the following parameters:

WRV=4,770, WUA=58, and DS=0.36.

EXAMPLE 3

The procedure is the same as in Example 2, but the reaction time is 15 minutes at a temperature of 120° C. The fiber material has the following parameters:

WRV=4,830, WUA=62, and DS=0.34.

Example 4

The procedure is the same as in Example 1, but the reaction time is 10 minutes at a temperature of 160° C. The fiber material has the following parameters:

WRV=4,680, WUA=60, and DS=0.33.

EXAMPLE 5

The procedure is the same as in Example 1, but in this case chemical reaction is carried out for 30 seconds in a microwave oven manufactured by Linde (®) Microtherm LMG 701). The fiber material has the following parameters:

WRV=10,350, WUA=57, and DS=0.29.

EXAMPLE 6

The procedure is the same as in Example 1, but in this case 25 g of the fibers are immersed in a solution composed of 49 g of NaOH, 72 g of Na-monochloroacetate, 2.44 g of bisacrylamido-acetic acid and 189 g of $H_2O$; the fibers are centrifuged to a reaction weight of 98.6 g. Chemical reaction is carried out on a sieve netting, using a stream of hot air at a temperature of 130° C., which is caused to act for 4 minutes. The fiber material has the following parameters:

WRV=5,150, WUA=59, and DS=0.49.

EXAMPLE 7

The procedure is the same as in Example 1, but in this case 20 g of the fibers are immersed in a solution composed of 52 g of NaOH, 89.98 g of acrylamide, 6.44 g of bisacrylamido-acetic acid, and 352 g of $H_2O$; the fibers are centrifuged to a reaction weight of 91 g. The reaction time is 15 minutes at a temperature of 120° C. The fiber material has the following parameters:

WRV=12,260 and WUA=44.

EXAMPLE 8

The procedure is the same as in Example 7, but the reaction time is 45 seconds in the microwave oven of Example 5. The fiber material has the following parameters:

WRV=7,800 and WUA=56.

EXAMPLE 9

The procedure is the same as in Example 7, but in this case 20 g of the fibers are immersed in a solution composed of 52.7 g of NaOH, 91.2 g of acrylamide, 6.5 g of bisacrylamido-acetic acid, and 356 g of $H_2O$; the fibers are centrifuged to a reaction weight of 84.7 g. The fiber material has the following parameters:

WRV=12,470 and WUA=24.9.

EXAMPLE 10

The procedure is the same as in Example 9, but chemical reaction is carried out for 45 seconds in the microwave oven. The fiber material has the following parameters:

WRV=2,670 and WUA=60.2.

EXAMPLE 11

2.5 kg of rayon staple fibers (1.7 dtex, length 40 mm) are immersed for 10 minutes at room temperature in a solution composed of 5.3 kg of a 50% concentration aqueous NaOH solution, 7.74 kg of Na-monochloroacetate, 0.263 kg of bisacrylamidoacetic acid and 18 kg of $H_2O$, and are then treated in a centrifuge to yield a reaction weight of 10.135 kg. To effect the actual chemical reaction, the mixture is filled into a polyethylene bag and stored for 60 minutes in a return-air drying chamber heated to 70° C. After neutralizing with glacial acetic acid, the reaction product is filtered and the solid residue is washed free from salt in an extraction column using an 80% by weight methanol. The fiber material which is dried at about 60° C. has the following parameters:

WRV=1,170, WUA=77, and DS=0.45.

EXAMPLE 12

The procedure is the same as in Example 11, but in this case a solution is used which is composed of 5.633 kg of a 50% concentration aqueous NaOH solution, 6.566 kg of Na-monochloroacetate, 0.279 kg of bisacrylamido-acetic acid, and 18.77 kg of H₂O; the fibers are centrifuged to a reaction weight of 7.8 kg. The fiber material has the following parameters:
WRV=3,270, WUA=74, and DS=0.31.

EXAMPLE 13

The procedure is the same as in Example 12, but chemical reaction is carried out for 26 hours at room temperature (23° C.). The parameters of the fiber material are indicative of a still incomplete reaction:
WRV=420, WUA=86, and DS=0.16.

EXAMPLE 14

7.6 g of a non-woven fabric consisting of 50% polyester fibers and 50% rayon staple fibers are immersed during 5 minutes at room temperature in a solution composed of 92.6 g of NaOH, 270 g of Na-monochloroacetate, 11.5 g of bisacrylamidoacetic acid, and 776 g of H₂O, and are then squeezed off to a reaction weight of 14.7 g. To effect the actual chemical reaction, the mixture is stored for 15 minutes in the drying chamber heated to about 130° C. After neutralizing with glacial acetic acid the reaction product is filtered, and the solid residue is washed in a 70% by weight aqueous isopropanol. After this treatment, the dried non-woven fabric has an absorption capacity for water of 2,680% by weight, as compared to 888% by weight prior to the treatment. The absorption capacity of the non-woven fabric is determined after applying H₂O to the sample up to saturation; it is related to the total weight of the non-woven fabric.

The following table gives the molar relationships for the participants in the reactions of Examples 1 to 13, as present in the materials squeezed off to reaction weight.

TABLE

| Example | Number of moles of reaction component: | | | | | |
|---|---|---|---|---|---|---|
| | cellulose hydrate | NaOH | H₂O | Na-monochloro-acetate | acrylamide | cross-linking agent |
| 1  | 1 | 0.85 | 12.7 | 0.85 | — | 0.02 |
| 2  | 1 | 0.90 | 15.3 | 0.90 | — | 0.02 |
| 3  | 1 | 0.85 | 12.7 | 0.85 | — | 0.02 |
| 4  | 1 | 0.85 | 12.7 | 0.85 | — | 0.02 |
| 5  | 1 | 0.85 | 12.7 | 0.85 | — | 0.02 |
| 6  | 1 | 1.98 | 17.0 | 1.00 | — | 0.02 |
| 7  | 1 | 1.59 | 23.8 | — | 1.55 | 0.04 |
| 8  | 1 | 1.59 | 23.8 | — | 1.55 | 0.04 |
| 9  | 1 | 1.92 | 28.8 | — | 1.87 | 0.04 |
| 10 | 1 | 1.92 | 28.8 | — | 1.87 | 0.04 |
| 11 | 1 | 1.12 | 16.8 | 1.12 | — | 0.02 |
| 12 | 1 | 1.00 | 17.0 | 0.80 | — | 0.02 |
| 13 | 1 | 1.00 | 17.0 | 0.80 | — | 0.02 |

It will be obvious to those skilled in the art that many modifications may be made within the scope of the present invention without departing from the spirit thereof, and the invention includes all such modifications.

What is claimed is:

1. A process for preparing swellable cross-linked carboxyalkylcelluloses in the form of fibers, by reacting cellulose, a carboxyalkylating etherifying agent, and a cross-linking agent in an aqueous alkaline medium, comprising effecting alkalizing, etherifying, and cross-linking simultaneously in one reaction step using fibers of cellulose hydrate or fiber-based textile sheet materials which contain these fibers, by contacting (a) said fibers or textile sheet materials which contain these fibers with an ample quantity of an aqueous alkaline reaction mixture, (b) removing part of the reaction mixture from the fibers or the textile sheet materials contacted therewith, so that at least the quantity required for reaction is still present, wherein the molar relationships of the components of said quantity of the reaction mixture range, relative to 1 mole of cellulose, from about 0.7 to 2.1 moles of alkali hydroxide, about 10 to 30 moles of H₂O, about 0.7 to 2 moles of the etherifying agent, and about 0.005 to 0.1 mole of the cross-linking agent, and (c) treating the fibers or the textile sheet materials containing said remainder of the aqueous alkaline reaction mixture with heat energy for the purpose of the actual chemical reaction.

2. A process according to claim 1 in which the etherification is a carboxymethylation with monochloroacetic acid or the salts thereof.

3. A process according to claim 1 in which the cross-linking is a reaction with phosphorus oxychloride, acrylamidomethylene chloroacetamide or with a compound which carries at least one of the following functional groups reactive towards hydroxyl groups:

the acrylamido group, R₁ being H or CH₃

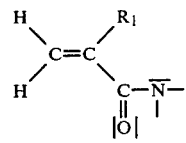

an α-halogenoepoxy group, Hal being Cl or Br

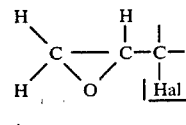

the chloroazomethine group

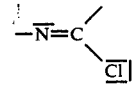

and the allyloxy-azomethine group

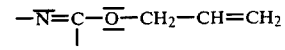

4. A process according to claim 1 in which the fibers or the textile sheet materials are contacted with the aqueous alkaline reaction mixture by spraying or immersing.

5. A process according to claim 1 in which the excess quantity of the reaction mixture is removed from the fibers or the textile sheet materials by squeezing off or centrifuging.

6. A process according to claim 1 in which, in the final reaction between the fibers or the textile sheet materials and the reaction mixture, heat energy is applied in the form of hot air or by a treatment with microwaves.

7. A process according to claim 1 in which the cellulose hydrate fibers used have lengths ranging from about 30 mm to about 150 mm.

* * * * *